US00PP36850P2

(12) United States Plant Patent
Grazzini

(10) Patent No.: US PP36,850 P2
(45) Date of Patent: Jul. 22, 2025

(54) ***ALLIUM* PLANT NAMED 'G22087'**

(50) Latin Name: *Allium schoenoprasum*
Varietal Denomination: G22087

(71) Applicant: Garden Genetics llc, Columbus, OH (US)

(72) Inventor: Richard A. Grazzini, Columbus, OH (US)

(73) Assignee: Garden Genetics, Columbus, OH (US)

( * ) Notice: Subject to any disclaimer, the term of this patent is extended or adjusted under 35 U.S.C. 154(b) by 0 days.

(21) Appl. No.: 19/025,328

(22) Filed: Jan. 16, 2025

(51) Int. Cl.
*A01H 5/02* (2018.01)
*A01H 6/04* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Cassandra Bright

(57) ABSTRACT

A new and distinct cultivar of *Allium* plant named 'G22087' is disclosed, characterized by large dark pink flowers held on stiff, thick flowering stems. Plants are stiffly upright with wider than average foliage for garden chives. Flowering occurs constantly through Summer. The new variety is an *Allium*, normally used for outdoor ornamental purposes.

2 Drawing Sheets

Figure 1:
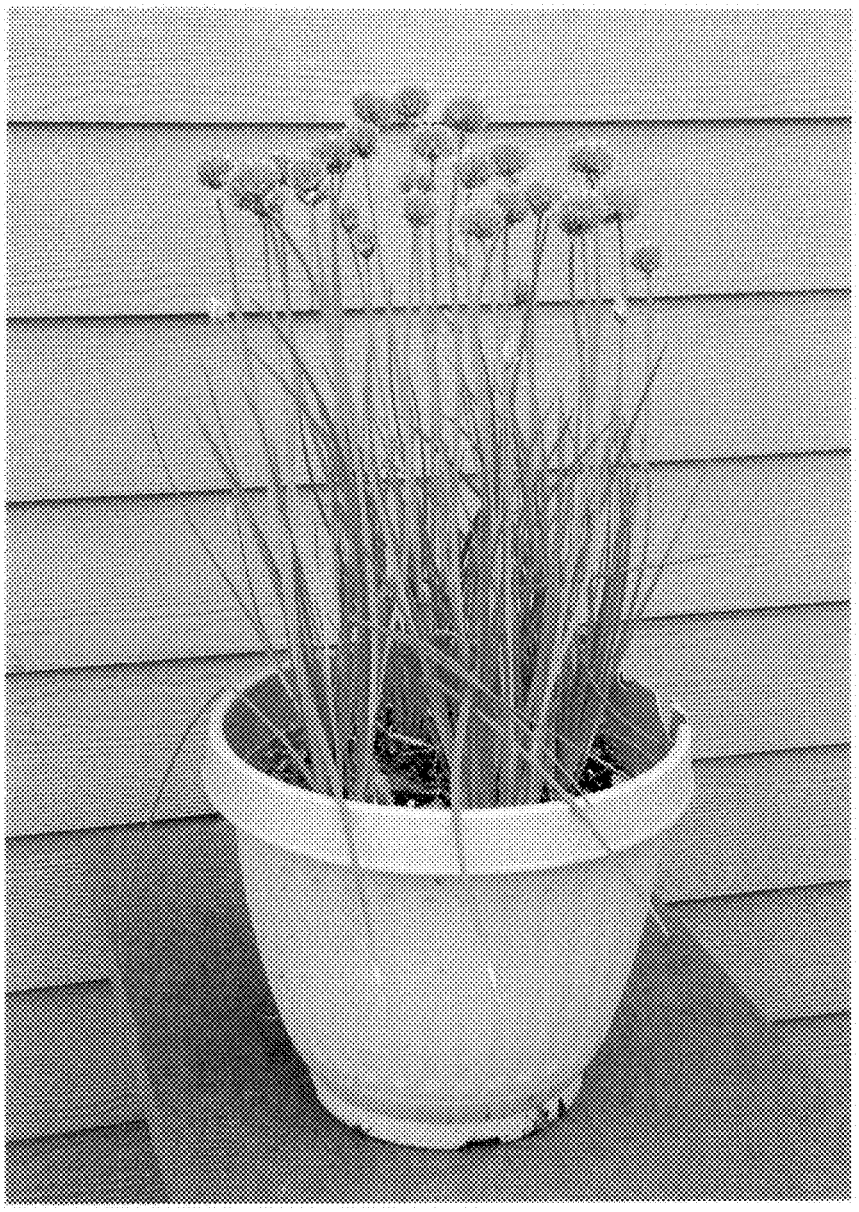

Latin name of the genus and species: *Allium schoenoprasum.*

Variety denomination: 'G22087'.

BACKGROUND OF THE INVENTION

The new *Allium* cultivar is a product of a planned breeding program conducted by the inventor at a research nursery in Bellefonte, Pennsylvania. The self-pollination resulting in this new variety was made in June of 2021.

The parent is the unpatented proprietary variety referred to as *Allium* 'G13-594'. The new variety was selected in August of 2022 by the inventor in a group of seedlings resulting from the 2021 self-pollination, in a nursery in Bellefonte, Pennsylvania.

Asexual reproduction of the new cultivar was performed by division, at the same nursery in Bellefonte, Pennsylvania during August of 2022, and has shown that the unique features of this cultivar are stable and reproduced true to type in multiple successive generations.

SUMMARY OF THE INVENTION

The cultivar 'G22087' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G22087'. These characteristics in combination distinguish 'G22087' as a new and distinct *Allium* cultivar:

1. Large, dark pink flowers.
2. Broad foliage, wider than typical for garden chives.
3. Stiffly upright habit.

4. Thick, stiff, upright flower stems.
5. Constant flowering though Summer.

PARENT COMPARISON

Plants of the new cultivar 'G22087' are similar to plants of the parent in most horticultural characteristics; however, plants of the new cultivar 'G22087' differ in the following:

1. 'G22087' is more uniform in leaf size than seed parent G13-594.
2. The foliage of 'G22087' is more glaucous blue-green in color than seed parent G13-594.
3. 'G22087' is more uniform in display of the desired upright habit than is G13-594.
4. 'G22087' is more vigorous and produces more divisions, more quickly than G13-594.
5. 'G22087' produces fewer seeds than G13-594 when self-pollinated. Neither variety produces many seeds when grown in isolation and self-pollinated, but new variety 'G22087' produces almost none, whereas breeding line G13-594 will routinely produce self-seed late in the season.

COMMERCIAL COMPARISONS

Plants of the new cultivar 'G22087' are comparable to the commercial variety *Allium* 'Dolores', unpatented and produced by seeds. The two *Allium* varieties are similar in most horticultural characteristics, however, the new variety 'G22087' differs in the following:

1. 'G22087' has larger, thicker broader leaves than 'Dolores'.
2. Leaves of 'G22087' leaves are more intensely glaucous-blue in color, compared to the medium green leaf color of the comparator 'Dolores'.
3. 'G22087' has more stiffly upright foliage than 'Dolores'.
4. 'G22087' has much larger flowers than 'Dolores'.
5. 'G22087' produces a more vigorous and larger plant than the comparator 'Dolores'.

Plants of the new cultivar 'G22087' are comparable to the unnamed, seed produced commercial garden *Allium* commonly found in the horticulture market. The new cultivar 'G22087' differs in the following:

1. 'G22087' has larger, longer leaves than common garden chive.
2. 'G22087' has thicker and broader leaves, and of a more glaucous blue-green color, than common garden chives.
3. 'G22087' has more stiffly upright foliage than do common garden chives.
4. 'G22087' displays larger, deeper lavender-pink flowers, and which remain healthy and in harvestable condition, than are available on common garden chives.
5. 'G22087' has more stiffly upright and thicker flower stems than does common garden chives.

BRIEF DESCRIPTION OF THE PHOTOGRAPHS

The accompanying photograph in FIG. 1 illustrates a typical flowering plant of 'G22087' grown outdoors in Columbus, OH at approximately 8-months old in a 1-gallon pot.

Figure 2:
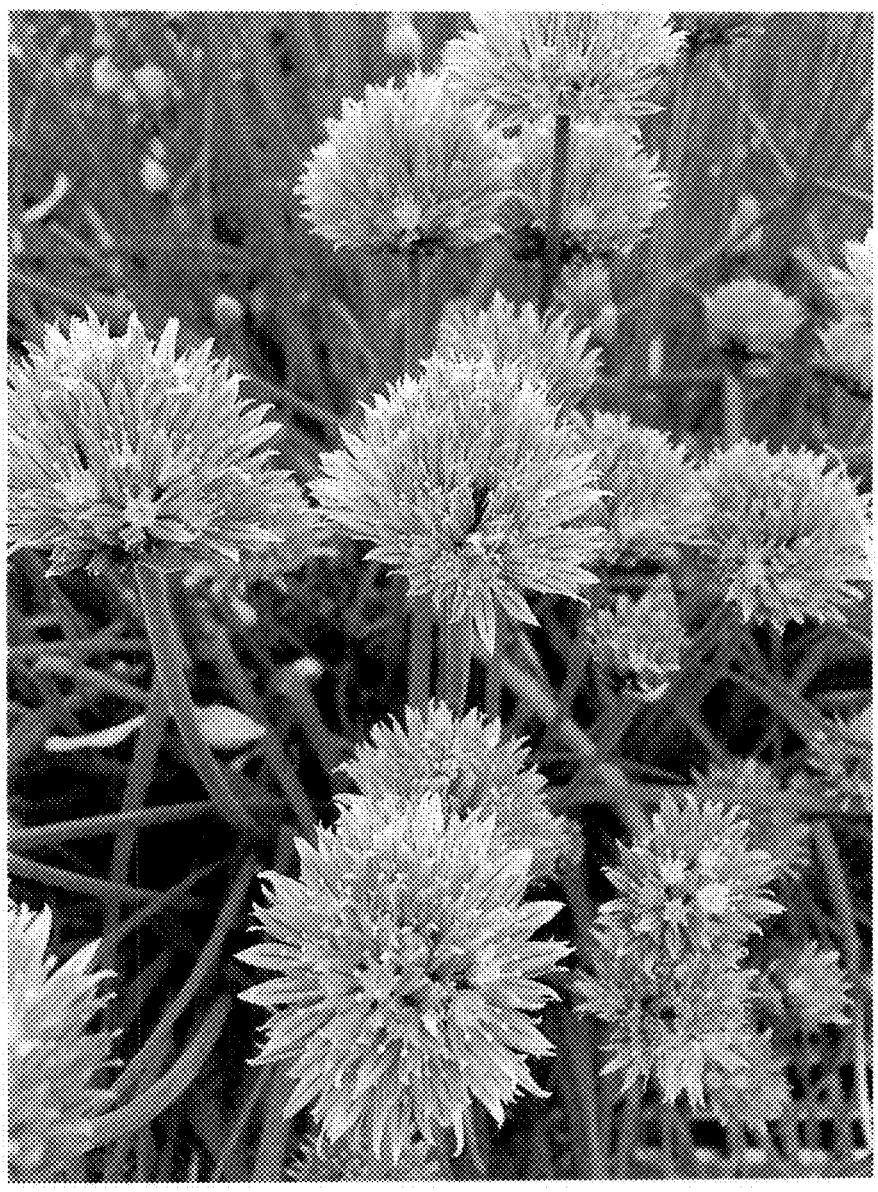

FIG. 2 illustrates a close-up view of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'G22087' plants grown outdoors in Camarillo, California. The growing temperature ranged from approximately 10° C. to 25° C. during the day and from approximately 6° C. to 12° C. during the night. General light conditions are normal sunlight and numerical values represent averages of typical plant types. Measurements were taken during June of 2024.

Botanical classification: *Allium schoenoprasum* 'G22087'.

ROOTS

Root description: Moderately, fleshy root system colored near Orange-White 159C and Yellow-White 158D. No rhizomes.

PROPAGATION

Typical method: Division or tissue culture.

PLANT

Growth habit: Clump forming flowering perennial with upright foliage.

Height: Foliar plane 22 cm. Flowering plane 22 cm.

Plant spread: Approximately 25 cm.

Growth rate: Moderate.

Growth pattern: Sessile rosulate foliage with no plant stem.

FOLIAGE

Leaf:

*Average leaf length*.—Approximately 17 to 20 cm.

*Average leaf width*.—Average range 4 to 6 mm.

*Arrangement*.—Basal, irregular whorls.

*Shape of blade*.—Linear in overall shape. Overall thin, hollow tube.

*Apex*.—Acute.

*Margin*.—Entire.

*Texture of top surface*.—Smooth.

*Texture of bottom surface*.—Smooth.

*Quantity of leaves clump*.—Average range 6 to 12.

*Color*.—Mature Upper surface: Near Green 137C with glaucous layer near Green 136C. 10% closest to base Green 141D. Mature Lower surface: Near Green 137C with glaucous layer near Green 136C. 10% closest to base Green 141D.

*Base*.—Truncate, non-clasping.

*Aspect*.—Upright.

*Foliage fragrance*.—Mild garlic scent when crushed.

FLOWER

Natural flowering season: Begins flowering in Spring in California.

Inflorescence type: Terminal Umbel with on average 25 to 40 flowers per umbel.

Individual flower type: Single.

Flower profile: Funnelform.

Lasting quality: Inflorescence shows no significant signs of aging for approximately 5 to 6 weeks.

Bud:

*Shape*.—Narrow ovate.

*Length*.—Approximately 8 mm.

*Diameter*.—Approximately 4 mm.

*Appearance*.—Shiny.

*Color*.—Near RHS Purple-Violet N82C, striped Violet 84A.

Umbel size:

*Diameter*.—Average 3.2 cm.

*Height*.—Average 2.2 cm.

Corolla:

*Arrangement*.—Apetalous, single, campanulate flowers composed of 6 basally fused tepals, shaped into a flared trumpet.

*Size*.—Length: Approximately 1.0 cm. Width: Approximately 1.0 cm at widest point. Lobe Length: Approximately 8 mm. Lobe Width: Average 3 mm.

Tepals:

*Margin*.—Entire.

*Shape*.—Lanceolate.

*Apex*.—Acute.

*Base*.—Fused.

*Appearance*.—Shiny.

*Texture*.—Glabrous all surfaces.

Color:

*Tepals*.—Opening: Outer surface: Near Violet-Purple N82B, center stripe Violet 83C. Inner surface: Near Violet-Purple N82B, center stripe Violet 83C. Mature: Outer surface: Near Violet 85C center stripe Purple-Violet N82A. Inner surface: Near Violet 85B center stripe Violet 83B.

Sepals: None.
Fragrance: Sweet, carnation-like scent.
Flower filament color: Near Violet 84D.
Flower anther color: Near Greyed-Purple N187D.
Anther quantity: 6, each approximately 1 mm long.
Stamen protrusion: No.
Pollen: Not observed.
Pistil:
*Number*.—1.
*Length*.—Approximately 5 mm.
*Style color*.—Near Greyed-Purple N187D.
*Stigma*.—Shape: Linear. Color: Near Greyed-Purple N187D.
*Ovary color*.—RHS Greyed-Green 190C.
Scape:
*Length*.—Average 17 cm.
*Diameter*.—4 to 6 mm.
*Texture*.—Glabrous.
*Color*.—Near Green 143C.
*Strength*.—Stiff and strong.
Pedicel:
*Length*.—5 to 7 mm.
*Diameter*.—About 1 mm.
*Texture*.—Glabrous. Color: Near Green 138A.

OTHER CHARACTERISTICS

Seeds: Very rarely produced. Small, black (203B) angular seeds around 1.5 mm in diameter.
Disease/pest resistance: Neither resistance nor susceptibility to normal diseases and pests of *Allium* observed.
Temperature range: USDA Zones 3-9.

What is claimed is:

1. A new and distinct cultivar of *Allium* plant named 'G22087' as herein illustrated and described.

* * * * *